United States Patent [19]

Effland et al.

[11] 4,268,515
[45] May 19, 1981

[54] SPIRO[DIHYDROBENZOFURAN-PIPERIDINES AND -PYRROLIDINES], PHARMACEUTICAL COMPOSITIONS THEREOF AND METHODS OF USE THEREOF

[75] Inventors: Richard C. Effland, Bridgewater; Larry Davis, Sergeantsville; Joseph T. Klein, Bridgewater, all of N.J.

[73] Assignee: Hoechst-Roussel Pharmaceuticals Inc., Somerville, N.J.

[21] Appl. No.: 118,146

[22] Filed: Feb. 4, 1980

[51] Int. Cl.³ ............... C07D 521/00; A61K 31/445; A61K 31/395
[52] U.S. Cl. ..................... 424/267; 546/17; 546/208; 260/326.5 CA; 260/326.34; 260/326.38; 260/326.4; 260/326.5 D; 260/326.5 A; 260/326.5 C
[58] Field of Search ............... 546/17; 260/326.5 CA, 260/326.34; 424/267, 274

[56] References Cited

U.S. PATENT DOCUMENTS

| | | | |
|---|---|---|---|
| 3,686,186 | 8/1972 | Houlihan et al. | 546/17 |
| 3,959,475 | 5/1976 | Bauer et al. | 424/267 |
| 3,962,259 | 6/1976 | Bauer et al. | 546/17 |
| 4,166,119 | 8/1979 | Effland et al. | 546/17 |
| 4,166,120 | 8/1979 | Effland et al. | 546/17 |

FOREIGN PATENT DOCUMENTS

7604352  11/1976  Netherlands ............... 546/17

OTHER PUBLICATIONS

Inubushi et al., Chemical and Pharmaceutical Bulletin (Japan), vol. 12, pp. 749–753 (1964).

*Primary Examiner*—Robert T. Bond
*Attorney, Agent, or Firm*—Jerome Rosenstock

[57] ABSTRACT

The invention relates to spiro[dihydrobenzofuran-piperidines and -pyrrolidines] of the formula

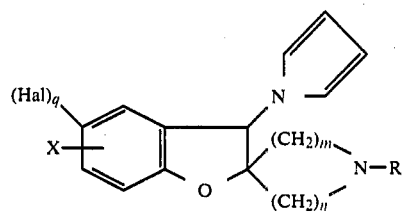

wherein R is the hydrogen atom, alkyl, alkoxycarbonyl, phenoxycarbonyl, cyano, aralkyl, alkanoyl, aralkanoyl, hydroxyalkyl, benzoylalkyl,

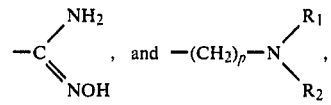

where p is an integer of 2 or 3 and $R_1$ and $R_2$ are the same or different and are hydrogen and alkyl; X is hydrogen and alkyl; Hal is a halogen and q is an integer of 0 or 1; m is an integer of 1 or 2, n is an integer of 1, 2 or 3, where the sum of m and n is 3 or 4; and the pharmaceutically acceptable acid addition salts thereof.

25 Claims, No Drawings

SPIRO[DIHYDROBENZOFURAN-PIPERIDINES AND-PYRROLIDINES], PHARMACEUTICAL COMPOSITIONS THEREOF AND METHODS OF USE THEREOF

To the best of our knowledge the compounds of the present invention have not heretofore been described or suggested. Spiro[phthalanpiperidine]s of the formula

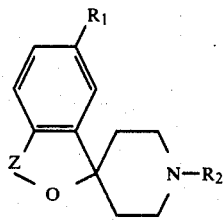

in which $R_1$ is hydrogen, loweralkyl, loweralkoxy, halogen or trifluoromethyl, $R_2$ is hydrogen or benzyl and Z is —$CH_2$— or —CO—, described by W. J. Houlihan et al. in U.S. Pat. No. 3,686,186, are outside the scope of this invention. The same applies to the natural product of the formula

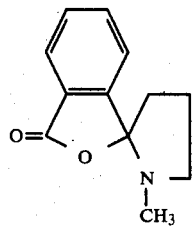

described by Y. Inubushi et al. [Chem. and Pharm. Bull (Japan) 12, 749 (1964)], as well as to substituted 1,3-dihydrospiro-(isobenzofuran)s of the formula

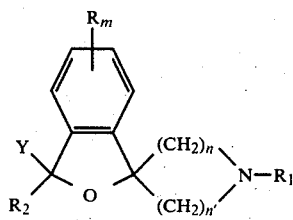

in which $R_m$ is hydrogen, alkyl, alkoxy, trifluoromethyl, halogen, hydroxy or methylenedioxy; $R_1$ is hydrogen, alkyl, cycloalkylalkyl, alkenyl, phenylalkyl, diphenylalkyl, diphenylmethoxyalkyl, alkanoyl, phenylalkanoyl, benzoyl, benzoylalkyl, phenylhydroxyalkyl, alkoxycarbonyl, phenyloxycarbonyl or cycloalkylcarbonyl; $R_2$ is alkyl or phenyl; Y is hydrogen, alkyl, alkoxy, hydroxy or phenyl and m, n and n' are integers from 1 to 3; and to 1,3-dihydrospiro-(isobenzofuran)s of the formula

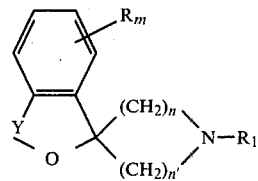

in which $R_m$ is hydrogen, alkyl, alkoxy, trifluoromethyl, halogen, hydroxy or methylenedioxy; $R_1$ is alkyl, cycloalkylalkyl, phenylalkyl, diphenylalkyl, diphenylmethoxyalkyl, alkanoyl, phenylalkanoyl, benzoylalkyl, phenylhydroxyalkyl or cycloalkylcarbonyl; Y is $CH_2$ or CO; m is 1 or 2 and n and n' are integers from 1 to 3, described by Victor J. Bauer and Raymond W. Kosley, Jr. in U.S. Pat. Nos. 3,959,475 and 3,962,259, respectively.

The compounds of the present invention have the general formula

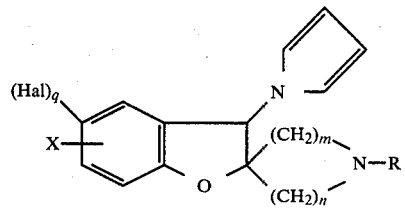

wherein R is the hydrogen atom, alkyl, alkoxycarbonyl, phenoxycarbonyl, cyano, aralkyl, alkanoyl, aralkanoyl, hydroxyalkyl, benzoylalkyl,

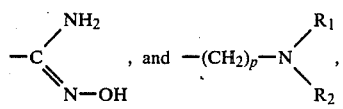

where p is an integer of 2 or 3, and $R_1$ and $R_2$ are the same or different and are hydrogen and lower alkyl; X is hydrogen and alkyl; Hal is a halogen; q is an integer of 0 or 1; m is an integer of 1 or 2, n is an integer of 1, 2 or 3, where the sum of m and n is 3 or 4.

In the above definitions the terms "alkyl," "alkoxy" or "alkanoyl" mean the group it is describing contains from 1 to 6 carbon atoms. The term "alkyl" refers to a straight or branched chain hydrocarbon containing no unsaturation; the term "alkoxycarbonyl" or "phenoxycarbonyl" refers to a monovalent substituent which consists of an alkoxy group or a phenoxy group, respectively, linked through a carbonyl group having its free valence bond from the carbon of the carbonyl group; the term "aralkyl" refers to a monovalent substituent which consists of an aryl group linked through an alkyl group having its free valence bond from a carbon of the alkyl group; the term "alkanoyl" refers to a monovalent substituent which consists of an alkyl group linked through a carbonyl group having its free valence bond from the carbon of the carbonyl group; the term "aralkanoyl" refers to a monovalent substituent which consists of an aryl group linked through an alkanoyl group, as defined above, having its free valence bond from the carbon of the carbonyl group; the term "benzoylalkyl" refers to a monovalent substituent which consists of the benzoyl group linked through an alkyl group having its free valence bond from a carbon of the alkyl group; the term "alkoxy" refers to a monovalent substituent which consists of an alkyl group linked through an ether oxygen having its free valence bond from the ether oxygen; and the term "halogen" refers to a member of the family consisting of fluorine, chlorine, bromine and iodine.

The compounds of the present invention are prepared in the following manner. The substituents R and X and the members m and n are as defined earlier with the exception that R is not hydrogen, cyano, benzoylalkyl or

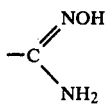

A halogen substituted benzyl pyrrole of the formula

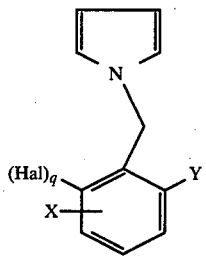

(I), where Y is a halogen selected from F, Cl, Br and I, typically prepared by reacting a 2-halobenzylamine of the formula

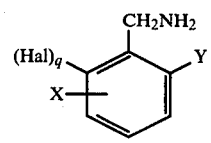

with 2,5-dimethoxytetrahydrofuran by heating at 80° to 120° C., in the presence of a suitable acid, such as acetic acid, is selected. Compound I is reacted with an organometallic compound, e.g., n-butyllithium, in a suitable dry, inert solvent, such as tetrahydrofuran, at reduced temperatures, e.g., −40° to −60° C., for two hours, followed by reaction with a substituted piperidone or pyrrolidone of the formula

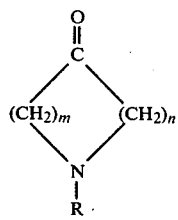

(II), e.g., 1-methyl-4-piperidone, at a temperature ranging from −60° C. to the reflux point of the solvent, for a period of time sufficient to form a novel piperidinol or a novel pyrrolidinol of the formula

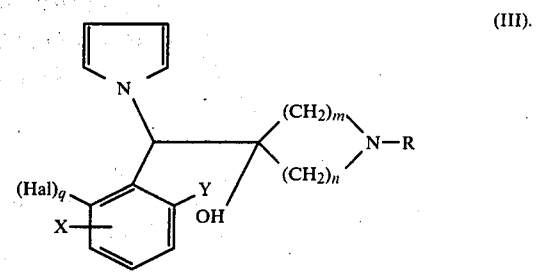

(III).

The compound III is reacted with a non-nucleophilic base in the presence of an inert solvent at a temperature of from 25° C. to the reflux point of the solvent to provide a compound of the invention of the structural formula

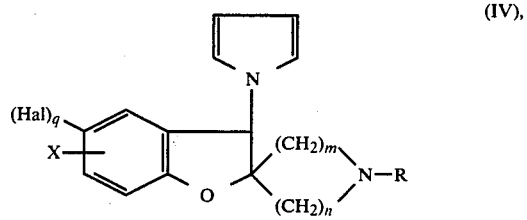

(IV), where R, X, m and n are as defined immediately above. In a preferred embodiment, sodium hydride is used as the base, dimethylformamide and benzene are used as a mixed solvent and the temperature is the reflux temperature of the solvent mixture.

A compound of formula IV in which R is aralkyl can be hydrogenated by any convenient method to provide the corresponding N-unsubstituted compound, i.e., where R is the hydrogen atom. A preferred method involves hydrogenation with a palladium on carbon catalyst.

Alternatively, a compound of formula IV can be treated with a chloroformate, such as a phenyl chloroformate or an alkyl chloroformate, in an inert solvent, such as dichloromethane, toluene or benzene, at a temperature of 25°–125° C. to provide the corresponding N-phenoxycarbonyl or N-alkoxycarbonyl, respectively, of the invention. Thereafter, the N-phenxoycarbonyl or N-alkoxycarbonyl compound of the invention is treated under reflux conditions with a base, e.g., an alkali metal hydroxide, such as NaOH, KOH, in a solvent such as water, an alcohol, e.g., ethanol, n-propanol, or with an acid such as hydrogen bromide in acetic acid to provide the compound of the invention where R is the hydrogen atom.

A compound of formula IV where R is alkyl or aralkyl is converted to a compound of the formula IV where R is cyano, by reacting with a suitable cyanogen halide, e.g., cyanogen bromide, in a solvent, e.g., chloroform, at a reflux temperature. The resulting cyano substituted compound is then reacted under basic conditions, in a suitable solvent, such as dimethylformamide with hydroxylamine hydrochloride at a temperature of from 80° to 110° C., to form a compound of the invention IV, where R is

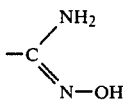

Alternatively, the resulting cyano substituted compound is hydrolyzed under acidic conditions to form a compound of the invention IV, where R is hydrogen.

An N-unsubstituted compound of the invention IV (R is hydrogen) can be reacted in a known fashion with an alkylhalide, aralkylhalide, ethylene glycol ketal, a benzoylalkylhalide or a dialkylaminoalkylhalide to provide the corresponding N-substituted compound of the invention IV in which the N-substituent (R) is alkyl, aralkyl, benzoylalkyl or dialkylaminoalkyl. Typically, the N-unsubstituted compound IV is reacted with the selected halide in an alcoholic solvent, e.g., n-butanol, in the presence of a base e.g., Na$_2$CO$_3$, and KI at a temperature ranging up to the reflux temperature of the solvent.

An N-unsubstituted compound of the invention IV (R is hydrogen) can be reacted in a known fashion with an alkoxycarbonylhalide, a phenoxycarbonylhalide, an alkanoylhalide or an aralkylanoylhalide, to form the corresponding N-substituted compound of the invention IV in which the N-substituent (R) is alkoxycarbonyl, phenoxycarbonyl, alkanoyl or aralkanoyl. A solvent such as dichloromethane or chloroform is typically used in this reaction. The use of an acid scavenger such as sodium bicarbonate, potassium carbonate or triethylamine is optional. The reaction temperature can vary from 0° C. to the reflux point of the solvent. Reflux conditions usually enhance the rate of the reaction. The resulting compound can then be conventionally reduced, using, for example, LiAlH$_4$ or BH$_3$ to reduce the carbonyl group contained therein.

Some novel compounds III useful in the preparation of the compounds IV of the invention are the following:
4-[(o-fluorophenyl)-(1-pyrryl)methyl]-1-methyl-4-piperidinol
1-benzyl-3-[(o-fluorophenyl)-(1-pyrryl)methyl]-3-pyrrolidinol
4-[(5-chloro-o-fluorophenyl)-(1-pyrryl)methyl]-1-methyl-4-piperidinol The spiro[dihydrobenzofuran-piperidine and pyrrolidines] are useful as antihypertensive agents due to their ability to depress blood pressure in mammals. Antihypertensive activity is measured in the spontaneous hypertensive rat by the indirect tail cuff method described in "Methods in Pharmacology," A. Schwartz, Ed., Vol. I, Appleton-Century Crofts, New York, New York, 1971, p. 135. In this procedure a group of five animals are treated orally for three days with the test compound in relation to the control group of the same number. The drop in blood pressure is measured on the third day following administration. The antihypertensive activities of some of the compounds, expressed as mm decrease in mean arterial blood pressure are given in Table I.

TABLE 1

| Compound | Dose mg/kg of body weight | Decrease in Blood Pressure mm/Hg |
|---|---|---|
| 2,3-dihydro-1'-methyl-3-(1-pyrryl)-spiro(benzofuran-2,4'-piperidine) hydrochloride | 10 | 50 |

TABLE 1-continued

| Compound | Dose mg/kg of body weight | Decrease in Blood Pressure mm/Hg |
|---|---|---|
|  | 5 | 30 |
| 2,3-dihydro-1'-phenethyl-3-(1-pyrryl)-spiro(benzofuran-2,4'-piperidine)oxalate Hemihydrate | 50 | 59 |
|  | 25 | 36 |
|  | 5 | 26 |
| 2,3-dihydro-3-(1-pyrryl)spiro(benzofuran-2,4'-piperidine)oxalate | 25 | 49 |
| 2,3-dihydro-1'-[3-(p-fluorobenzoyl)-propyl]-3-(1-pyrryl)spiro(benzofuran-2,4'-piperidine)oxalate | 10 | 51 |
| 1'-cyano-2,3-dihydro-3-(1-pyrryl)spiro-(benzofuran-2,4'-piperidine) | 50 | 29 |
| 1'-(2-diethylaminoethyl)-2,3-dihydro-3-(1-pyrryl)spiro(benzofuran-2,4'-piperidine]-dioxalate | 50 | 38 |
| 2,3-dihydro-3-(1-pyrryl)spiro(benzofuran-2,4'-piperidine)-1'-carboxamidoxime | 50 | 44 |
| 2,3-dihydro-3-(1-pyrryl)spiro(benzofuran-2,3'-pyrrolidine)maleate | 50 | 58 |
|  | 5 | 15 |
| 1'-benzyl-2,3-dihydro-3-(1-pyrryl)spiro(benzofuran-2,3'pyrrolidine)oxalate | 50 | 42 |
| α-methyl dopa | 50 | 40 |

Blood pressure reduction is achieved when the compounds of the invention are administered to a subject requiring such treatment at an effective oral, parenteral or intravenous dose of from 0.1 to 50 mg/kg of body weight per day. A preferred effective dose within this range is from about 0.1 to 5 mg/kg of body weight per day. A particularly preferred effective amount is about 1 mg/kg of body weight per day. It is to be understood, however, that for any particular subject, specific dosage regimens should be adjusted according to the individual need and the professional judgement of the person administering or supervising the administration of the compounds of the invention. It is to be further understood that the dosages set forth herein are examples only and that they do not, to any extent, limit the scope or practice of the invention.

The compounds of the invention are also useful as analgesic agents due to their ability to aleviate pain in mammals. The activity of the compound is demonstrated in the 2-phenyl-1,4-benzoquinone-induced writhing test in mice, a standard assay for analgesia [Proc. Soc. Exptl. Biol. Med., 95, 729 (1975)]. The analgesic activity of some of the compounds expressed in terms of percent inhibition of writhing are given in Table II.

TABLE II

| Compound | Dose mg/kg of body weight | Inhibition in Writhing % |
|---|---|---|
| 2,3-dihydro-1'-phenethyl-3-(1-pyrryl)-spiro(benzofuran-2,4'-piperidine)oxalate hemihydrate | 1.1* | 50 |
|  | 8.7** | 50 |
| 2,3-dihydro-1'-phenacetyl-3-(1-pyrryl)-spiro(benzofuran-2,4'-piperidine) | 25* | 60 |
| 2,3-dihydro-1'-propyl-3-(1-pyrryl)spiro-(benzofuran-2,4'-piperidine)oxalate | 25* | 42 |
| 2,3-dihydro-1'-[3-(p-fluorobenzoyl)propyl]-3-(1-pyrryl)spiro(benzofuran-2,4'-piperidine)-oxalate | 4.9* | 50 |
| 2,3-dihydro-3-(1-pyrryl)spiro(benzofuran-2,4'-piperidine)oxalate | 25* | 61 |
| 1-benzyl-2,4-dihydro-3-(1-pyrryl)spiro- | | |

TABLE II-continued

| Compound | Dose mg/kg of body weight | Inhibition in Writhing % |
|---|---|---|
| (benzofuran-2,3'-pyrrolidine)oxalate | 25* | 56 |
| aspirin | 53** | 50 |

*subcutaneous dose
**oral dose

The analgesic relief of pain is achieved when the compounds of the invention are administered to a subject requiring such treatment at an effective oral, parenteral or intravenous dose of from 0.1 to 25 mg/kg of body weight per day. A preferred effective dose within this range is from about 1 to 10 mg/kg of body weight per day. A particularly preferred effective amount is about 2 mg/kg of body weight per day. It is to be understood, however, that for any particular subject, specific dosage regimens should be adjusted according to the individual need. It is further to be understood that the dosages set forth herein are examples only and that they do not, to any extent, limit the scope of practice of the invention.

Examples of some of the compounds of the invention are:

2,3-dihydro-1'-methyl-3-(1-pyrryl)spiro(benzofuran-2,3'-piperidine);
2,3-dihydro-1'-n-hexyl-3-(1-pyrryl)spiro(benzofuran-2,4'-piperidine);
2,3-dihydro-1'-propyl-3-(1-pyrryl)spiro(benzofuran-2,3'-piperidine);
2,3-dihydro-1'-n-hexyl-3-(1-pyrryl)spiro(benzofuran-2,3'-pyrrolidine);
2,3-dihydro-1'-methyl-3-(1-pyrryl)spiro(benzofuran-2,3'-pyrrolidine);
2,3-dihydro-1'-phenoxycarbonyl-3-(1-pyrryl)spiro(benzofuran-2,3'-piperidine);
2,3-dihydro-1'-phenoxycarbonyl-3-(1-pyrryl)spiro(benzofuran-2,3'-pyrrolidine);
2,3-dihydro-3-(1-pyrryl)spiro(benzofuran-2,3'-piperidine);
2,3-dihydro-1'-phenethyl-3-(1-pyrryl)spiro(benzofuran-2,3'-piperidine):
2,3-dihydro-1'-phen-n-pentyl-3-(1-pyrryl)spiro(benzofuran-2,4'-piperidine);
2,3-dihydro-1'-phenacetyl-3-(1-pyrryl)spiro(benzofuran-2,3'-piperidine);
2,3-dihydro-1'-phenbutyryl-3-(1-pyrryl)spiro(benzofuran-2,4'-piperidine);
2,3-dihydro-1'-phenvaleryl-3-(1-pyrryl)spiro(benzofuran-2,4'-piperidine);
2,3-dihydro-1'-phenacetyl-3-(1-pyrryl)spiro(benzofuran-2,3'-pyrrolidine);
2,3-dihydro-1'-phenpropionyl-3-(1-pyrryl)spiro(benzofuran-2,3'-pyrrolidine);
2,3-dihydro-1'-[3-(p-fluorobenzoyl)propyl]-3-(1-pyrryl)-spiro(benzofuran-2,3'-piperidine);
2,3-dihydro-1'-[2-benzoylbutyl]-3-(1-pyrryl)spiro(benzofuran-2,4'-piperidine);
2,3-dihydro-1'-[2-benzoylethyl]-3-(1-pyrryl)spiro(benzofuran-2,3'-pyrrolidine);
2,3-dihydro-1'-[3-benzoyl-(3-methyl)-pentyl]-3-(1-pyrryl)-spiro(benzofuran-2,3'-pyrrolidne);
1'-cyano-2,3-dihydro-3-(1-pyrryl)spiro(benzofuran-2,3'-piperidine);
1'-cyano-2,3-dihydro-3-(1-pyrryl)spiro(benzofuran-2,3'-pyrrolidine);
2,3-dihydro-N-hydroxy-3-(1-pyrryl)spiro(benzofuran-2,3'-piperidine)-1'-carboximidamide
2,3-dihydro-N-hydroxy-3-(1-pyrryl)spiro(benzofuran-2,3'-pyrrolidine)-1'-carboximidamide
2,3-dihydro-1'-ethoxycarbonyl-3-(1-pyrryl)spiro(benzofuran-2,3'-piperidine);
2,3-dihydro-1'-n-hexoxycarbonyl-3-(1-pyrryl)spiro(benzofuran-2,4'-piperidine);
2,3-dihydro-1'-propoxycarbonyl-3-(1-pyrryl)spiro(benzofuran-2,3'-piperidine);
2,3-dihydro-1'-methoxycarbonyl-3-(1-pyrryl)spiro(benzofuran-2,3'-pyrrolidine);
2,3-dihydro-1'-butoxycarbonyl-3-(1pyrryl)spiro(benzofuran-2,3'pyrrolidine);
2,3-dihydro-1'-acetyl-3-(1-pyrryl)spiro(benzofuran-2,4'-piperidine);
2,3-dihydro-1'-acetyl-3-(1-pyrryl)spiro(benzofuran-2,3'-piperidine);
2,3-dihydro-1'-butyryl-3-(1-pyrryl)spiro(benzofuran-2,3'-pyrrolidine);
5-chloro-2,3-dihydro-1'-methyl-3-(1-pyrryl)spiro(benzofuran-2,4'-piperidine)
2,3-dihydro-5-fluoro-1'-methyl-3-(1-pyrryl)spiro(benzofuran-2,3'-pyrrolidine);
2,3-dihydro-5-fluoro-1'-methyl-3-(1-pyrryl)spiro(benzofuran-2,3'-piperidine);
2,3-dihydro-5-ethyl-1'-methyl-3-(1-pyrryl)spiro(benzofuran-2,4'-piperidine);
2,3-dihydro-4-methyl-1'-phenoxycarbonyl-3-(1-pyrryl)-spiro(benzofuran-2,4'-piperidine);
5-bromo-2,3-dihydro-1'-methyl-3-(1-pyrryl)spiro(benzofuran-2,3'-pyrrolidine);
2,3-dihydro-5-fluoro-1'-phenoxycarbonyl-3-(1-pyrryl)-spiro(benzofuran-2,4'-piperidine);
2,3-dihydro-5-fluoro-1-phenoxycarbonyl-3-(1-pyrryl)-spiro(benzofuran-2,4'-piperidine);
5-chloro-2,3-dihydro-1'-phenoxycarbonyl-3-(1-pyrryl)-spiro(benzofuran-2,3'-piperidine);
2,3-dihydro-5-fluoro-3-(1-pyrryl)spiro(benzofuran-2,4'-piperidine);
5-bromo-2,3-dihydro-1'-phenoxycarbonyl-3-(1-pyrryl)-spiro(benzofuran-2,3'-pyrrolidine);
2,3-dihydro-5-ethyl-1'-methyl-3-(1-pyrryl)spiro)(benzofuran-2,3'-pyrrolidine);
2,3-dihydro-6-methyl-3-(1-pyrryl)spiro(benzofuran-2,3'-pyrrolidine);
2,3-dihydro-5-fluoro-3(1-pyrryl)spiro(benzofuran-2,3'-piperidine);
5-chloro-2,3-dihydro-3-(1-pyrryl)spiro(benzofuran-2,4'-piperidine);
5-bromo-2,3-dihydro-2,3-dihydro-3-(1-pyrryl)spiro(-benzofuran-2,3'-pyrrolidine);
2,3-dihydro-5-fluoro-1'-phenethyl-3-(1-pyrryl)spiro(-benzofuran-2,4'-piperidine);
5-bromo-2,3-dihydro-1'-phenethyl-3-(1-pyrryl)spiro(-benzofuran-2,3'-piperidine);
5-chloro-2,3-dihydro-1'-phenethyl-3-(1-pyrryl)spiro(-benzofuran-2,3'-pyrrolidine);
2,3-dihydro-5-fluoro-1'-phenacetyl-3-(1-pyrryl)spiro(-benzofuran-2,4'-piperidine);
2,3-dihydro-5-ethyl-1'-phenacetyl-3-(1-pyrryl)spiro(-benzofuran-2,4'-piperidine);
5-bromo-2,3-dihydro-5-fluoro-1'-phenacetyl-3-(1-pyrryl)spiro(benzofuran-2,3'-piperidine);
5-chloro-2,3-dihydro-1'-phenacetyl-3-(1-pyrryl)spiro(-benzofuran-2,3'-pyrrolidine);
5-bromo-2,3-dihydro-1'-(3-benzoylpropyl)-3-(1-pyrryl)-spiro(benzofuran-2,4'-piperidine);

2,3-dihydro-5-fluoro-1'-(3-benzoylpropyl)-3-(1-pyrryl)-spiro(benzofuran-2,3'-pyrrolidine);

5-chloro-2,3-dihydro-1'-(3-benzoylpropyl)-3-(1-pyrryl)-spiro(benzofuran-2,3'-piperidine);

1'-cyano-2,3-dihydro-5-fluoro-3-(1-pyrryl)spiro(benzofuran-2,3'-pyrrolidine);

1'-cyano-2,3-dihydro-6-methyl-3-(1-pyrryl)spiro(benzofuran-2,4'-piperidine);

2,3-dihydro-N-hydroxy-5-bromo-3-(1-pyrryl)spiro(benzofuran-2,3'-pyrrolidine)-1-carboximidamide 2,3-dihydro-N-hydroxy-5-fluoro-3-(1-pyrryl)spiro(benzofuran-2,3'-piperidine)-1-carboximidamide;

5-bromo-2,3-dihydro-4-methyl-1'-(3-benzoylpropyl)-3-(1-pyrryl)spiro(benzofuran-2,3'-piperidine);

5-bromo-2,3-dihydro-N-hydroxy-3-(1-propyl)spiro(-benzofuran-2,3'-pyrrolidine)-1'-carboximidamide;

5-chloro-2,3-dihydro-1'-ethoxycarbonyl-3-(1-pyrryl)-spiro(benzofuran-2,4'-piperidine);

1'-butoxycarbonyl-5-bromo-2,3-dihydro-3-(1-pyrryl)-spiro(benzofuran-2,3'-piperidine);

1'-acetyl-5-chloro-2,3-dihydro-3-(1-pyrryl)spiro(benzofuran-2,4'-piperidine);

1'-acetyl-2,3-dihydro-5-bromo-3-(1-pyrryl)spiro(benzofuran-2,3'-pyrrolidine);

1'-butoxycarbonyl-5-butyl-2,3-dihydro-3-(1-pyrryl)-spiro(benzofuran-2,3'-piperidine);

1'-acetyl-2,3-dihydro-5-methyl-3-(1-pyrryl)spiro(benzofuran-2,3'-pyrrolidine);

2,3-dihydro-5-fluoro-1'-valeryl-3-(1-pyrryl)spiro(benzofuran-2,3'-piperidine);

5-bromo-2,3-dihydro-1'-(3-benzoylbutyl)-3-(1-pyrryl)-spiro(benzofuran-2,3'-pyrrolidine);

1'-cyano-2,3-dihydro-5-fluoro-3-(1-pyrryl)spiro(benzofuran-2,4'-piperidine);

5-chloro-1'-cyano-2,3-dihydro-3-(1-pyrryl)spiro(benzofuran-2,3'-piperidine);

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphonic, perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the spiro [benzofuran piperidine or pyrrolidine] of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the spiro[dihydrobenzofuranpiperidine or pyrrolidine] of the invention.

The tablets, pills, capsules, troches and the like may also contain the following adjuvants; a binder such as microcrystalline cellulose, gum tragacanth or gelatin; and excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the spiro[dihydrobenzofuran piperidine or pyrrolidine] of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the spiro[dihydrobenzofuran piperidine or pyrrolidine] of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLE I a.

4-[(o-Fluorophenyl)-(1-pyrryl)methyl]-1-methyl-4-piperidinol hydrochloride

To a solution of 1-(o-fluorobenzyl)pyrrole (20.0 g) in 100 ml of dry tetrahydrofuran, cooled to −60° C., is added a solution of n-butyllithium (60 ml, 0.13 mole) over a period of 30 minutes. The mixture is stirred at −60° C. for 1 hour, at ambient temperature for 1 hour, then a solution of 1-methyl-4-piperidone (11.3 g) in 50 ml of dry tetrahydrofuran is added over a period of 30 minutes. After refluxing at 65° C. for 20 hours, the mixture is cooled, poured into 900 ml water, stirred for 1 hour, then extracted with ether. The ether layer is washed twice with water and then dried (saturated NaCl, anhydrous $MgSO_4$). After filtering, the solvent is evaporated to an oil, which is converted by treatment with ethereal HCl to give 12.0 g of an HCl-salt. The salt is recrystallized from ethyl acetate/methanol/ether to yield 10.0 g of 4-[(o-fluorophenyl)-(1-pyrryl)methyl]-1-methyl-4-piperidinol hydrochloride, 135° C. dec.

Analysis:
Calculated for $C_{17}H_{21}FN_2O \cdot HCl$: 62.85%C; 6.83%H; 8.63%N. Found: 62.16%C; 7.01%H; 9.06%N.

b.

2,3-Dihydro-1'-methyl-3-(1-pyrryl)spiro(benzofuran-2,4'-piperidine)hydrochloride To a suspension of NaH (50% in oil, 0.6 g) in 50 ml of dry benzene is added a solution of 4-[(o-fluorophenyl)-1-pyrryl)methyl]-1-methyl-4-piperidinol (of Example 1a, 3.0 g, 0.01 mole) in 50 ml dry benzene. The mixture is heated to reflux, then 20 ml of dimethylformamide is added and reflux is continued for 3 and ½ hours. After cooling, the mixture is poured into 300 ml water, stirred for 15 minutes, then extracted with ether. The organic layers are washed twice with water and then dried (saturated NaCl, anhydrous $MgSO_4$). After filtering, the solvents are evaporated to an oil comprising 2,3-dihydro-1'-methyl-3-(1-pyrryl)spiro(benzofuran-2,4'-piperidine) which is converted by treatment with ethereal HCl to yield 0.5 g of a hydrochloride, salt, mp 85° C. This material is recrystallized from ethyl acetate to yield 0.3 g of 2,3-dihydro-1'-methyl-3-(1-pyrryl)spiro(-benzofuran-2,4'-piperidine)hydrochloride, mp 217°–219° C.

Analysis:
Calculated for $C_{17}H_{20}N_2O \cdot HCl$: 66.98%C; 6.95%H; 9.19%N. Found: 67.02%C; 7.42%H; 8.98%N.

EXAMPLE II 2,3-Dihydro-1'-phenoxycarbonyl-3-(1-pyrryl)spiro(-benzofuran-2,4'-piperidine To a cold solution of 14.0 g of 2,3-dihydro-1'-methyl-3-(1-pyrryl)spiro(benzofuran-2,4'-piperidine), of Example Ib, in 100 ml dichloromethane is added dropwise a solution of 9.4 g of phenyl chloroformate in 25 ml of dichloromethane. After stirring at ambient temperature for 24 hours, the solvent is evaporated to an oil, which solidifies to a solid upon trituration with hexane to yield 16.7 g (85%) of the product, 2,3-dihydro-1'-phenoxycarbonyl-3-(1-pyrryl)spiro(benzofuran-2,4'-piperidine), mp 115°–118° C. The material is recrystallized from ethyl acetate to yield 14.0 g of the product 2,3-dihydro-1'-phenoxycarbonyl-3-(1-pyrryl)spiro(benzofuran-2,4'-piperidine), mp 140°–145° C.

Analysis:
Calculated for $C_{23}H_{22}N_2O_3$: 73.77%C; 5.92%H; 7.48%N. Found: 73.58%C; 6.01%H; 7.41%N.

EXAMPLE III 2,3-Dihydro-3-(1-pyrryl)spiro(benzofuran-2,4'-piperidine)oxalate

To a solution of 20.0 g of potassium hydroxide in 100 ml of n-propanol and 6 ml of water is added a solution of 15.5 g of 2,3-dihydro-1'-phenoxycarbonyl-3-(1-pyrryl)spiro(benzofuran-2,4'-piperidine) of Example II in 150 ml n-propanol. After stirring at reflux for 24 hours, the mixture is cooled and the solvent is evaporated to an oil. The oil is stirred with 300 ml of water for 15 minutes and then extracted with chloroform. The chloroform layer is washed twice with water and then dried (saturated NaCl, anhydrous $MgSO_4$). After filtering, the solvent is evaporated to an oil comprising 2,3-dihydro-3-(1-pyrryl)spiro(benzofuran-2,4'-piperidine) which is dissolved in ether, filtered and then converted to an oxalate salt with an ethereal oxalic acid solution to yield 10.6 g (75%) of the oxalate salt, mp 95° C. The compound is recrystallized from a 9:1 ethyl acetate/methanol solution to yield 8.5 g of 2,3-dihydro-3-(1-pyrryl)spiro(benzofuran-2,4'-piperidine)oxalate, 125° C. dec.

Analysis:
Calculated for $C_{16}H_{18}N_2O \cdot (CO_2H)_2$: 62.78%C; 5.85%H; 8.14%N. Found: 62.02%C; 5.83%H; 7.87%N.

EXAMPLE IV 2,3-Dihydro-1'ethoxycarbonyl-3-(1-pyrryl)spiro(benzofuran-2,4'-piperidine)

To a mixture of 15.5 g of 2,3-dihydro-1'-methyl-3-(1-pyrryl)spiro(benzofuran-2,4'-piperidine) of Example Ib and 25 g of $K_2CO_3$ in 200 ml of benzene is added a solution of 8.1 g of ethyl chloroformate in 50 ml of benzene. After stirring at reflux for 24 hours, the mixture is cooled, washed twice with water, thrice with dilute HCl solution, twice with water and is then dried (saturated NaCl, anhydrous $MgSO_4$). After filtering, the solvent is evaporated to an oil which solidifies upon trituration with hexanes to yield 7.4 g (40%) of a solid, mp 122°–124° C. A sample of this material is recrystallized twice from hexanes to yield a solid of 2,3-dihydro-1'-ethoxycarbonyl-3-(1-pyrryl)spiro(benzofuran-2,4'-piperidine), mp 132°–133° C.

Analysis:
Calculated for $C_{19}H_{22}N_2O_3$: 69.91%C; 6.80%H; 8.58%N. Found: 69.91%C; 6.83%H; 8.51%N.

EXAMPLE V

1'-Cyano-2,3-dihydro-3-(1-pyrryl)spiro(benzofuran-2,4'-piperidine)

To a refluxing mixture of 3.7 g of cyanogen bromide and 20.0 g of $K_2CO_3$ in 100 ml of chloroform is added a solution of 8.0 g of 2,3-dihydro-1'-methyl-3-(1-pyrryl)-spiro(benzofuran-2,4'-piperidine) of Example Ib in 75 ml of chloroform over a period of 30 minutes. After refluxing for 5 hours and standing at ambient temperature for 15 hours, the mixture is filtered and the filtrate evaporated to an oil which solidifies upon trituration with petroleum ether to yield 6.9 g (82%) of a solid, mp 140°–150° C. This material is recrystallized twice from 4:1 hexane/acetone to yield 5.8 g of 1'-cyano-2,3-dihydro-3-(1-pyrryl)spiro(benzofuran-2,4'-piperidine), mp 165°–168° C.

Analysis:
Calculated for $C_{17}H_{17}N_3O$: 73.09%C; 6.14%H; 15.04%N. Found: 72.95%C; 6.23%H; 15.23%N.

EXAMPLE VI 2,3-dihydro-N-hydroxy-3-(1-pyrryl)spiro(benzofuran-2,4'-piperidine)-1-carboximidamine To 20 ml of dry DMF is added 6.4 g of 1'-cyano-2,3-dihydro-3-(1-pyrryl)spiro(benzofuran-2,4'-piperidine) of Example IV, 2.6 g of hydroxylamine hydrochloride and 7.7 g of Na$_2$CO$_3$. The mixture is stirred at 105° C. for 1 and ½ hours, then 1.0 g of hydroxylamine hydrochloride is added and heating is continued for an additional 1 hour period. The mixture is cooled, poured into 500 ml of iced-water, stirred for 15 minutes and the resultant precipitate is collected, washed with water then dried (60° C. for 2 hours, vacuum dessicator for 16 hours) to yield 5.1 g (71%) of product, 75° C. dec. The resultant solid is recrystallized twice from 4:1 hexane/ether solution to yield 3.8 g of 2,3-dihydro-N-hydroxy-3-(1-pyrryl)spiro(benzofuran-2,4′-piperidine)-1-carboximidamide, 160° C. dec.

Analysis:

Calculated for C$_{17}$H$_{20}$N$_4$O$_2$: 65.36%C; 6.45%H; 17.94%N. Found: 65.74%C; 6.44%H; 17.60%N.

EXAMPLE VII 2,3-Dihydro-1′-[3-(p-fluorobenzoyl)propyl]-3-(1-pyrryl)spiro(benzofuran-2,4′-piperidine)oxalate To 100 ml of n-butanol is added 4.5 g of 2,3-dihydro-3-(1-pyrryl)spiro(benzofuran-2,4′-piperidine) of Example III, 4.9 g of γ-chloro-p-fluorobutyrophenone ethylene glycol ketal, 20.0 g of anhydrous K$_2$CO$_3$ and 100 mg of KI. After stirring at reflux for 2 days, the mixture is cooled, filtered and the solvent evaporated to an oil. The oil is dissolved in a solution of 100 ml of ethanol and 100 ml of 3 N HCl and refluxed for 1 hour. After cooling, the mixture is poured into 300 ml of water, stirred for 10 minutes, the pH adjusted to 12 with NaOH solution and then extracted with benzene. The benzene extract is washed thrice with water and then dried (saturated NaCl, anhydrous MgSO$_4$). After filtering, the solvent is evaporated to an oil which is dissolved in ether, then converted to an oxalate salt with ethereal oxalic acid solution to yield 7.1 g (77%) of the oxalate salt, mp 90° C. The oxalate salt is recrystallized twice from ethyl acetate to yield 5.2 g of 2,3-dihydro-1′-[3-(p-fluorobenzoyl)propyl]-3-(1-pyrryl)spiro(benzofuran-2,4′-piperidine)oxalate, mp 120° C.

Analysis:

Calculated for C$_{26}$H$_{27}$FN$_2$O$_2$.(CO$_2$H)$_2$: 66.13%C; 5.75%H; 5.51%N. Found: 65.97%C; 5.87%H; 5.77%N.

EXAMPLE VIII

1′-(Diethylaminoethyl)-2,3-dihydro-3-(1-pyrryl)spiro(benzofuran-2,4′-piperidine)dioxalate To 100 ml of n-butanol is added 4.5 g of 2,3-dihydro-3-(1-pyrryl)spiro(benzofuran-2,4′-piperidine) of Example III, 2.7 g of 2-diethylaminoethyl chloride, 20.0 g of anhydrous K$_2$CO$_3$, and 100 mg of KI. After stirring at reflux for 48 hours, the mixture is cooled, filtered and the solvent evaporated to an oil. The oil is stirred with 500 ml of water for 15 minutes and is then extracted with ether. The ether extract is washed with water and then dried (saturated NaCl, anhydrous MgSO$_4$). After filtering, the solvent is evaporated to an oil which is converted with ethereal oxalic acid solution to yield 8.0 g (83%) of the dioxalate salt, mp 75° C. The dioxalate is recrystallized twice from ethyl acetate to yield 5.5 g of 1′-(2-diethylaminoethyl)-2,3-dihydro-3-(1-pyrryl)-spiro(benzofuran-2,4′-piperidine)-dioxalate, mp 115° C.

Analysis:

Calculated for C$_{22}$H$_{31}$N$_3$O.2(CO$_2$H)$_2$: 58.52%C; 6.61%H; 7.88%N. Found: 58.17%C; 6.79%H; 7.83%N.

EXAMPLE IX 2,3-Dihydro-1′-phenacetyl-3-(1-pyrryl)spiro(benzofuran-2,4′-piperidine)

To a cold solution of 5.2 g of 2,3-dihydro-3-(1-pyrryl)spiro(benzofuran-2,4′-piperidine) of Example III and triethylamine (3.2 ml, 0.025 mole) in 100 ml dry dichloromethane is added a solution of phenacetyl chloride (3.4 ml, 0.025 mole) in 25 ml dry dichloromethane. After stirring at ambient temperature for 24 hours, the mixture is washed twice with water and then dried (saturated NaCl, anhydrous MgSO$_4$). After filtering, the solvent is evaporated to an oil which solidified to yield 7.0 g (92%) of a solid, mp 130° C., upon trituration with petroleum ether. The material is recrystallized twice from a 1:1 ethyl acetate/hexane solution to yield 6.0 g of 2,3-dihydro-1′-phenacetyl-3-(1-pyrryl)spiro(benzofuran-2,4′-piperidine), mp 160°–163° C.

Analysis:

Calculated for C$_{24}$H$_{24}$N$_2$O$_2$: 77.39%C; 6.49%H; 7.52%N. Found: 77.10%C; 6.55%H; 7.26%N.

EXAMPLE X 2,3-Dihydro-1′-phenethyl-3-(1-pyrryl)spiro(benzofuran-2,4′-piperidine) oxalate hemihydrate To a refluxing suspension of LiAlH$_4$ (1.52 g) in 100 ml dry tetrahydrofuran, is added a solution of 7.0 g of 2,3-dihydro-1′-phenacetyl-3-(1-pyrryl)spiro(benzofuran-2,4′-piperidine) of Example IX in 50 ml dry tetrahydrofuran. After refluxing at 70° C. for 20 hours, the mixture is cooled, quenched with 60 ml saturated NH$_4$Cl solution, diluted with 100 ml of ether and then filtered. The organic phase is collected, washed twice with water and then dried (saturated NaCl, anhydrous MgSO$_4$). After filtering the solvents are evaporated to an oil which is converted to an oxalate salt by treatment with ethereal oxalic acid solution to yield 5.1 g (56%) of the oxalate, mp 100° C. The material is recrystallized twice from ethyl acetate to yield 3.5 g of 2,3-dihydro-1′-phenethyl-3-(1-pyrryl)spiro(benzofuran-2,4′-piperidino)oxalate hemihydrate, mp 115° C.

Analysis:

Calculated for C$_{24}$H$_{26}$N$_2$O.(CO$_2$H)$_2$.½ H$_2$O: 68.40%C; 6.40%H; 6.14%N. Found: 68.75%C; 6.22%H; 6.40%N.

EXAMPLE XI 2,3-Dihydro-1′-propyl-3-(1-pyrryl)spiro(benzofuran-2,4′-piperidine)oxalate To a cold solution of 3.1 g of 2,3-dihydro-3-(1-pyrryl)spiro(benzofuran-2,4′-piperidine) of Example III and triethylamine (2.5 ml, 0.015 mole) in 100 ml dry dichloromethane is added dropwise, a solution of 1.4 g of propionyl chloride in 50 ml of dichloromethane. After stirring at ambient temperature for 24 hours, the mixture is washed with water and then dried (saturated NaCl, anhydrous MgSO$_4$). After filtering, the solvent is evaporated to yield 4.0 g of an oil. The oil is dissolved in 60 ml of dry tetrahydrofuran (THF) and then added to a refluxing suspension of 1.14 g of LiAlH$_4$ in 100 ml dry THF. After refluxing at 65° C. for 24 hours, the mixture is cooled, quenched with 60 ml saturated NH$_4$Cl solution, diluted with ether and filtered. The organic layer is collected, washed with water and then dried (saturated NaCl, anhydrous MgSO$_4$). After filtering the solvents are evaporated to an oil which is dissolved in ether, then converted, as described above in Example VIII, to 2.7 g of an oxalate salt, 100° C. dec. The oxalate is recrystallized twice from ethyl acetate to yield 2.1 g of 2,3-dihydro-1'-propyl-3-(1-pyrryl)spiro(benzofuran-2,4'-piperidine)oxalate, 130° C. dec.

Analysis:

Calculated for $C_{19}H_{24}N_2O.(CO_2H)_2$: 65.26%C; 6.78%H; 7.25%N. Found: 64.91%C; 6.69%H; 7.36%H.

EXAMPLE XII a.

1-Benzyl-3-[(o-fluorophenyl)-(1-pyrryl)methyl]-3-pyrrolidinol

To a solution of 124.0 g. of 1-(o-fluorobenzyl)pyrrole of Example Ia in 400 ml THF at −80° C. is added n-butyllithium (22% in hexane, 320 ml, 0.74 mole) dropwise, with stirring, over a period of about 1 hour. After stirring at −80° C. for 1 additional hour, a solution of 124.0 g of 1-benzyl-3-pyrrolidine in 100 ml THF is added over a period of 30 minutes. The mixture is then stirred at −80° C. for 1 hour, then at ambient temperature for 3 hours. After standing 16 hours at ambient temperature, the mixture is poured into 1500 ml of water, stirred for 15 minutes, the THF layer collected and the aqueous portion extracted with two 250 ml portion of ether. The combined ether/THF layers are washed with two 500 ml portions of water and dried (saturated NaCl solution, anhydrous $MgSO_4$). After filtering, the solvents are evaporated to yield 240 g of an oil, which is overlaid with hexanes at 5° C. for 16 hours to yield 144 g (58%) of a solid, mp 65°–70° C. A portion of the solid is recrystallized twice from petroleum ether to yield a solid, mp 87°–89° C. of 1-benzyl-3-[(o-fluorophenyl)-(1-pyrryl)methyl]3-pyrrolidinol.

Analysis:

Calculated for $C_{22}H_{23}FN_2O$: 75.40%C; 6.61%H; 8.00%N. Found: 75.51%C; 6.66%H; 7.94%N.

b.

1'-Benzyl-2,3-dihydro-3-(1-pyrryl)spiro(benzofuran-2,3'-pyrrolidine)oxalate

To a suspension of NaH (50% in oil, treated with hexanes, 7.2 g) in 50ml of benzene is added a solution of 44.0 g of 1-benzyl-3-[(o-fluorophenyl)-(1-pyrryl)methyl]-3-pyrrolidinol of Example XIIa in 200 ml of benzene. The mixture is heated to reflux, then 175 ml DMF is added and reflux is continued for 5 hours. After cooling, the mixture is poured into 800 ml of water, stirred for 15 minutes and then extracted with ether. The ether layer is collected and then extracted with three 200 ml portions of 3 N HCl solution. The aqueous acidic layer is basified with $Na_2CO_3$ and then extracted with ether. The ether layer is washed with water, then dried (saturated NaCl, anhydrous $MgSO_4$). After filtering, the solvent is evaporated to yield 14 g (35%) of an oil, comprising 1'-benzyl-2,4-dihydro-3-(1-pyrryl)spiro(benzofuran-2,3'-pyrrolidine). A sample of the oil is redissolved in ether and then converted, as in Example VIII, to yield 4.0 g of an oxalate salt, 85° C. dec. The material is recrystallized twice from (4:1) ethyl acetate/methanol solution to yield 2.5 g of a solid, 136°–138° C. dec. of 1-benzyl-2,3-dihydro-3-(1-pyrryl)spiro(benzofuran-2,3'-pyrrolidine)oxalate.

Analysis:

Calculated for $C_{22}H_{22}N_2O.(CO_2H)_2$: 68.56%C; 5.75%H; 6.66%N. Found: 68.36%C; 5.70%H; 6.64%N.

EXAMPLE XIII

2,3-Dihydro-3-(1-pyrryl)spiro(benzofuran-2,3'-pyrrolidine)maleate

To 400 ml of toluene is added 33.0 g of 1'-benzyl-2,3-dihydro-3-(1-pyrryl)spiro(benzofuran-2,3'-pyrrolidine), of Example XIIb, 50 g of anhydrous $K_2CO_3$ and a solution of 10.8 g of ethyl chloroformate in 50 ml of toluene. After stirring at 80° C. for 4 hours, the mixture is cooled, diluted with 200 ml of ether, washed with water, washed with 3 N HCl solution, washed with water and then dried (saturated NaCl solution, anhydrous $MgSO_4$). After filtering, the solvents are evporated to yield 24 g (75%) of an oil. The oil is dissolved in 250 ml of n-propanol and then added to a solution of 25 g of potassium hydroxide in 25 ml of water. After stirring at reflux (100° C.) for 7 hours, the mixture is cooled, the solvents evaporated to a semi-solid which is stirred with 500 ml of water for 10 minutes and then extracted with ether. The ether extract is washed with water and then extracted with 3 N HCl solution. The aqueous acidic extract is basified with $Na_2CO_3$ to pH 10 and then extracted with a 2:1 ether/toluene solution. The organic layer is washed with water and then dried (saturated NaCl, anhydrous $MgSO_4$). After filtering, the solvents are evaporated to yield 4.1 g (30%) of a solid, mp 120°–128° C. which is dissolved in ether, converted to the maleate salt by treatment with an etheral solution of maleic acid to yield 6.7 g of the maleate, 150° C. dec. The maleate is recrystallized twice from 3:1 ethyl acetate/methanol solution to yield a solid, 161°–163° C. dec of 2,3-dihydro-3-(1-pyrryl)spiro(benzofuran-2,3'-pyrrolidine)maleate.

Analysis:

Calculated for $C_{15}H_{16}N_2O.C_4H_4O_4$: 64.03%C; 5.66%H; 7.86%N. Found: 63.93%C; 5.40%H; 7.66%N.

EXAMPLE XIV

2,3-Dihydro-1'-ethyl-3-(1-pyrryl)spiro(benzofuran-2,4'-piperidine)oxalate

To 100 ml of dichlormethane is added 5.5 g of 2,3-dihydro-3-(1-pyrryl)-spiro(benzofuran-2,4'-piperidine) of Example III and triethylamine (3.8 ml, 0.025 mole). The mixture is cooled with an ice-bath, then a solution of acetyl chloride (1.8 ml, 0.025 mole) in 30 ml dichloromethane is added over a period of ten minutes. After stirring at ambient temperature for 20 hours, the mixture is evaporated to a semi-solid, which is stirred with 50 ml water, then extracted into ether/ethyl acetate. The organic solution is washed with water, 2 N HCl solution, water, then dried (saturated NaCl, anhydrous $MgSO_4$). After filtering, the solvents are evaporated to a semi-solid, 4.8 g (84%), mp 45° C. The resultant semi-solid is dissolved in 60 ml dry THF, then added to a cold suspension of lithium aluminum hydride (1.33 g) in 100 ml dry THF. After stirring at ambient temperature for 20 hours, the mixture is cooled, quenched with 15 ml saturated $NH_4Cl$ solution, diluted with ether, filtered, and the organic layer is washed with water and then dried (saturated NaCl, anhydrous $MgSO_4$). After filtering, the solvents are evaporated to an oil, which is dissolved in ether and then converted to the oxalate salt using the procedure of Example VIII to yield 3.0 g of a solid, 80° C. dec. This material is recrystallized twice from ethyl acetate/methanol/ether, to yield 2.5 g (60%) mp 115°–118° C. of 2,3-dihydro-1'-ethyl-3-(1-pyrryl)-spiro(benzofuran-2,4'-piperidine)oxalate.

Analysis:
Calculated for $C_{18}H_{22}N_2O \cdot C_2H_2O_4$ 64.50%C; 6.5%H; 7.52%N. Found: 64.43% C; 6.40%H; 7.31%N.

EXAMPLE XV 2,3-Dihydro-1'-(2-hydroxyethyl)-3-(1-pyrryl)spiro(benzofuran-2,4'-piperidine)

A mixture of 6 g 2,3-dihydro-3-(1-pyrryl)spiro(benzofuran-2,4'-piperidine) of Example III, ethyl bromoacetate (4.6 g), sodium bicarbonate (20 g) and 100 mg of potassium iodide in DMF (50 ml) is stirred at 70° C. for one hour.

The mixture is cooled, filtered and concentrated to an oil which is stirred with water and extracted with an ether-ethyl acetate mixture. The organic layer is washed with water, dried (saturated NaCl, anhydrous $MgSO_4$), filtered and concentrated to give 5 g (62%) of an oil comprising a desired ester intermediate.

A solution of the ester (5 g, 15 mmole) in THF (50 ml) is added to a cooled suspension of $LiAlH_4$ (1.1 g) in THF (100 ml). After the addition is completed the mixture is warmed to ambient temperature.

The reaction mixture is again cooled, diluted with ether and quenched by slow addition of saturated $NH_4Cl$. The mixture is then filtered, washed with water, dried (saturated NaCl, anhydrous $MgSO_4$), filtered and concentrated to give an oil (3.5 g, 80%) which is distilled via Kugelrohr apparatus to yield 2.5 g of a glass, b.p. 200°–210°/0.4 mm, comprising 2,3-dihydro-1'-(2-hydroxyethyl)-3-(1-pyrryl)spiro(benzofuran-2,4'-piperidine).

We claim:
1. A compound depicted by the formula

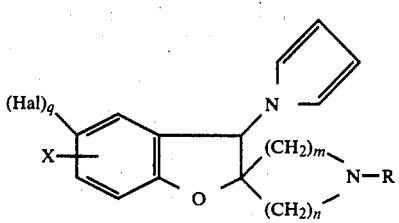

wherein R is hydrogen, alkyl of 1 to 6 carbon atoms, alkoxycarbonyl where the alkoxy moiety has 1 to 6 carbon atoms, phenoxycarbonyl, cyano, phenylalkyl where the alkyl moiety has 1 to 6 carbon atoms, alkanoyl of 1 to 6 carbon atoms, phenylalkanoyl where the alkanoyl moiety has 1 to 6 carbon atoms, hydroxyalkyl of 1 to 6 carbon atoms, benzoylalkyl where the alkyl moiety has 1 to 6 carbon atoms,

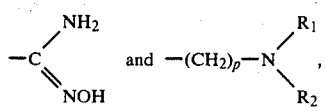

where p is an integer of 2 or 3; and $R_1$ and $R_2$ are the same or different and are hydrogen and lower alkyl of 1 to 6 carbon atoms; X is hydrogen and alkyl of 1 to 6 carbon atoms; Hal is halogen; q is an integer of 0 or 1; m is an integer of 1 or 2 and n is an integer of 1, 2 or 3 where the sum of m and n is 3 or 4; and the pharmaceutically acceptable acid addition salts thereof.

2. The compound as defined in claim 1 wherein R is hydrogen.

3. The compound as defined in claim 1 wherein R is alkyl.

4. The compound as defined in claim 1 wherein m is 2 and the sum of m and n is 4.

5. The compound as defined in claim 4 which is 2,3-dihydro-1'-methyl-3-(1-pyrryl)spiro(benzofuran-2,4'-piperidine) or a pharmaceutically acceptable acid addition salt thereof.

6. The compound as defined in claim 4 which is 2,3-dihydro-1'-phenoxycarbonyl-3-(1-pyrryl)spiro(benzofuran-2,4'-piperidine) or a pharmaceutically acceptable acid addition salt thereof.

7. The compound as defined in claim 4 which is 2,3-dihydro-3-(1-pyrryl)spiro(benzofuran-2,4'-piperidine) or a pharmaceutically acceptable acid addition salt thereof.

8. The compound as defined in claim 4 which is 2,3-dihydro-1'-ethoxycarbonyl-3-(1-pyrryl)spiro(benzofuran-2,4'-piperidine) or a pharmaceutically acceptable acid addition salt thereof.

9. The compound as defined in claim 4 which is 1'-cyano-2,3-dihydro-3-(1-pyrryl)spiro(benzofuran-2,4'-piperidine) or a pharmaceutically acceptable acid addition salt thereof.

10. The compound as defined in claim 4 which is 2,3-dihydro-N-hydroxy-3-(1-pyrryl)spiro(benzofuran-2,4'-piperidine)-1'-carboximidamide or a pharmaceutically acceptable acid addition salt thereof.

11. The compound as defined in claim 4 which is 2,3-dihydro-1'-[3-(p-fluorobenzoyl)propyl]-3-(1-pyrryl)spiro(benzofuran-2,4'-piperidine) or a pharmaceutically acceptable acid addition salt thereof.

12. The compound as defined in claim 4 which is 1'-(2-diethylaminoethyl)-2,3-dihydro-3-(1-pyrryl)-spiro(benzofuran-2,4'-piperidine) or a pharmaceutically acceptable acid addition salt thereof.

13. The compound as defined in claim 4 which is 2,3-dihydro-1'-phenacetyl-3-(1-pyrryl)spiro(benzofuran-2,4'-piperidine) or a pharmaceutically acceptable acid addition salt thereof.

14. The compound as defined in claim 4 which is 2,3-dihydro-1'-phenethyl-3-(1-pyrryl)spiro(benzofuran-2,4'-piperidine) or a pharmaceutically acceptable acid addition salt thereof.

15. The compound as defined in claim 4 which is 2,3-dihydro-1'-propyl-3-(1-pyrryl)spiro(benzofuran-2,4'-piperidine) or a pharmaceutically acceptable acid addition salt thereof.

16. The compound as defined in claim 4 which is 2,3-dihydro-1'-ethyl-3-(1-pyrryl)spiro(benzofuran-2,4'-piperidine) or a pharmaceutically acceptable acid addition salt thereof.

17. The compound as defined in claim 4 which is 2,3-dihydro-1'-(2-hydroxyethyl)-3-(1-pyrryl)spiro(benzofuran-2,4'-piperidine) or a pharmaceutically acceptable acid addition salt thereof.

18. The compound as defined in claim 1 wherein m is 1 and the sum of m and n is 4.

19. The compound as defined in claim 1 wherein the sum of m and n is 3.

20. The compound as defined in claim 18 which is 1'-benzyl-2,3-dihydro-3-(1-pyrryl)spiro(benzofuran-2,3'-pyrrolidine) or a pharmaceutically acceptable acid addition salt thereof.

21. The compound as defined in claim 18 which is 2,3-dihydro-3-(1-pyrryl)spiro(benzofuran-2,3'-pyrrolidine) or a pharmaceutically acceptable acid addition salt thereof.

22. A blood pressure reducing composition which comprises an inert blood pressure reducing adjuvant and an amount effective in reducing blood pressure of a compound of the formula

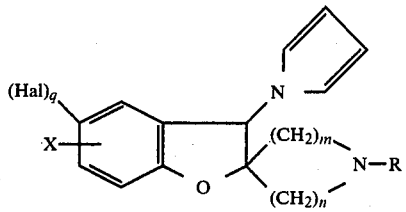

wherein R is hydrogen, alkyl of 1 to 6 carbon atoms, alkoxycarbonyl where the alkoxy moiety has 1 to 6 carbon atoms, phenoxycarbonyl, cyano, phenylalkyl where the alkyl moiety has 1 to 6 carbon atoms, alkanoyl of 1 to 6 carbon atoms, phenylalkanoyl where the alkanoyl moiety has 1 to 6 carbon atoms, hydroxyalkyl of 1 to 6 carbon atoms, benzoylalkyl where the alkyl moiety has 1 to 6 carbon atoms,

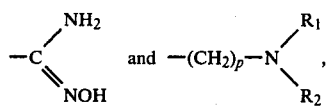

where p is an integer of 2 or 3 and $R_1$ and $R_2$ are the same or different and are hydrogen and lower alkyl of 1 to 6 carbon atoms; X is hydrogen and alkyl of 1 to 6 carbon atoms; Hal is halogen; q is an integer of 0 or 1; m is an integer of 1 or 2 and n is an integer of 1, 2 or 3, where the sum of m and n is 3 or 4; and the pharmaceutically acceptable acid addition salts thereof.

23. An analgesic composition which comprises an inert adjuvant and an effective pain alleviating amount of a compound of the formula

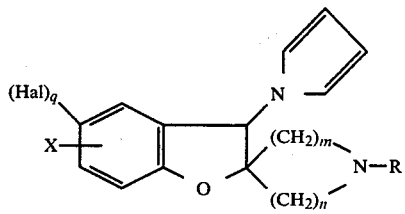

wherein R is hydrogen, alkyl of 1 to 6 carbon atoms, alkoxycarbonyl where the alkoxy moiety has 1 to 6 carbon atoms, phenoxycarbonyl, cyano, aralkyl where the alkyl moeity has 1 to 6 carbon atoms, alkanoyl of 1 to 6 carbon atoms, aralkanoyl where the alkanoyl moiety has 1 to 6 carbon atoms, hydroxyalkyl of 1 to 6 carbon atoms, benzoylalkyl where the alkyl moiety has 1 to 6 carbon atoms,

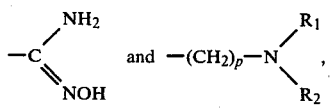

where p is an integer of 2 or 3 and $R_1$ and $R_2$ are the same or different and are hydrogen and lower alkyl of 1 to 6 carbon atoms; X is hydrogen and alkyl of 1 to 6 carbon atoms; Hal is halogen; q is an integer of 0 or 1; m is an integer of 1 or 2 and n is an integer of 1, 2 or 3, where the sum of m and n is 3 or 4; and the pharmaceutically acceptable acid addition salts thereof.

24. A method of reducing blood pressure in mammals comprising administering to a mammal a blood pressure reducing effective amount of a compound of the formula

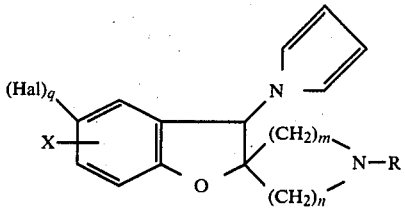

wherein R is hydrogen, alkyl of 1 to 6 carbon atoms, alkoxycarbonyl where the alkoxy moiety has 1 to 6 carbon atoms, phenoxycarbonyl, cyano, phenylalkyl where the alkyl moiety has 1 to 6 carbon atoms, alkanoyl of 1 to 6 carbon atoms, phenylalkanoyl where the alkanoyl moiety has 1 to 6 carbon atoms, hydroxyalkyl of 1 to 6 carbon atoms, benzoylalkyl where the alkyl moiety has 1 to 6 carbon atoms,

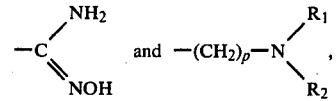

where p is an integer of 2 or 3 and $R_1$ and $R_2$ are the same or different and are hydrogen and lower alkyl of 1 to 6 carbon atoms; X is hydrogen and alkyl of 1 to 6 carbon atoms, Hal is halogen; q is an integer of 0 or 1; m is an integer of 1 or 2 and n is an integer of 1, 2 or 3, where the sum of m and n is 3 or 4; and the pharmaceutically acceptable acid addition salts thereof.

25. A method of alleviating pain in a mammal which comprises administering to a mammal a pain alleviating effective amount of a compound of the formula

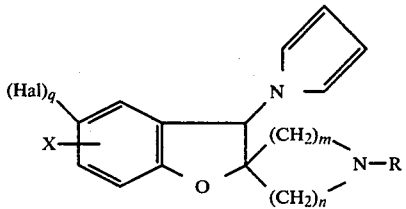

wherein R is hydrogen, alkyl of 1 to 6 carbon atoms, alkoxycarbonyl where the alkoxy moiety has 1 to 6 carbon atoms, phenoxycarbonyl, cyano, phenylalkyl where the alkyl moiety has 1 to 6 carbon atoms, alkanoyl of 1 to 6 carbon atoms, phenylalkanoyl where the alkanoyl moiety has 1 to 6 carbon atoms, hydroxyalkyl of 1 to 6 carbon atoms, benzoylalkyl where the alkyl moiety has 1 to 6 carbon atoms,

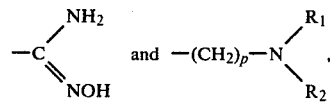

where p is an integer of 2 or 3 and $R_1$ and $R_2$ are the same or different and are hydrogen and lower alkyl of 1 to 6 carbon atoms; X is hydrogen and alkyl of 1 to 6 carbon atoms; Hal is halogen; q is an integer of 0 or 1, m is an integer of 1 or 2 and n is an integer of 1, 2 or 3, where the sum of m and n is 3 or 4; and the pharmaceutically acceptable acid addition salts thereof.

* * * * *

UNITED STATES PATENT AND TRADEMARK OFFICE
CERTIFICATE OF CORRECTION

PATENT NO. : 4,268,515

DATED : May 19, 1981

INVENTOR(S) : Effland et al.

It is certified that error appears in the above—identified patent and that said Letters Patent is hereby corrected as shown below:

| | |
|---|---|
| Column 7, lines 57-58: | "...pyrryl)-spiro..." should be --...pyrryl)spiro...--; |
| Column 7, lines 63-64: | "...pyrryl)-spiro..." should be --...pyrryl)spiro...--; |
| Column 8, line 43: | "...spiro)(benzo..." should be --...spiro(benzo...--; |
| Column 8 line 47: | "...fluoro-3(1-pyrryl..." should be --...fluoro-3-(1-pyrryl...--; |
| Column 8, line 51: | "5-bromo-2,3-dihydro-2,3-dihydro-3-..." should be --5-bromo-2,3-dihydro-3-; |
| Column 9, line 15: | "...3-(1-propyl)..." should be --...3-(1-pyrryl)...--; |
| Column 9, lines 50-51: | "phosphonic" should be --phosphoric--; |
| Column 12, line 22: | "2,3-Dihydro-1'ethoxy..." should be --2,3-Dihydro-1'-ethoxy...--; |
| Column 13, line 16: | "65.74%C" should be --65.47%C--; |
| Column 13, line 48: | "1'-(Diethyl..." should be --1'-(2-Diethyl...--; |
| Column 14, line 14: | "solidified" should be --solidifies--; |
| Column 14, line 42: | "...piperidino)..." should be --...piperidine)...--; |

UNITED STATES PATENT AND TRADEMARK OFFICE
CERTIFICATE OF CORRECTION

PATENT NO. : 4,268,515

DATED : May 19, 1981

INVENTOR(S) : Effland et al.

It is certified that error appears in the above—identified patent and that said Letters Patent is hereby corrected as shown below:

Column 15, line 26:  "portion" should be --portions--;

Column 15, line 58:  "1'-benzyl-2,4-..." should be --1'-benzyl-2,3-...--;

Column 17, line 3:  "6.5%H" should be --6.50% H--;

Claim 23, line 50:  "6L" should be --6--

Signed and Sealed this

Eleventh Day of August 1981

[SEAL]

Attest:

Attesting Officer

GERALD J. MOSSINGHOFF

Commissioner of Patents and Trademarks